(12) United States Patent
Tamir et al.

(10) Patent No.: US 10,376,364 B2
(45) Date of Patent: Aug. 13, 2019

(54) IMPLANT DELIVERY CAPSULE

(71) Applicant: Edwards Lifesciences Corporation, Irvine, CA (US)

(72) Inventors: Ilan Tamir, Hefzi-Bah (IL); Noam Nir, Gesher Haziv (IL); Boaz Manash, Givat Ada (IL); David Maimon, Haifa (IL); Oren Cohen, Kadima (IL)

(73) Assignee: Edwards Lifesciences Corporation, Irvine, CA (US)

( * ) Notice: Subject to any disclaimer, the term of this patent is extended or adjusted under 35 U.S.C. 154(b) by 228 days.

(21) Appl. No.: 15/344,163

(22) Filed: Nov. 4, 2016

(65) Prior Publication Data

US 2017/0128205 A1    May 11, 2017

Related U.S. Application Data

(60) Provisional application No. 62/253,464, filed on Nov. 10, 2015.

(51) Int. Cl.
*A61F 2/24*    (2006.01)

(52) U.S. Cl.
CPC .......... *A61F 2/2436* (2013.01); *A61F 2/2439* (2013.01)

(58) Field of Classification Search
CPC ........ A61F 2/24; A61F 2/2427; A61F 2/2436; A61F 2/2439
See application file for complete search history.

(56) References Cited

U.S. PATENT DOCUMENTS

| 3,409,013 A | 11/1968 | Berry |
| 3,472,230 A | 10/1969 | Fogarty |

(Continued)

FOREIGN PATENT DOCUMENTS

| CN | 2855366 Y | 1/2007 |
| DE | 2246526 A1 | 3/1973 |

(Continued)

OTHER PUBLICATIONS

Int'l. Search Report for PCT/US2016/060914, completed Feb. 9, 2017.

(Continued)

*Primary Examiner* — Tuan V Nguyen
(74) *Attorney, Agent, or Firm* — Meunier Carlin & Curfman LLC

(57) ABSTRACT

Disclosed herein are embodiments of delivery capsules for delivering prosthetic implants around the relatively tight bends of a catheter. In particular, disclosed herein are delivery capsules including a tubular layer for holding the heart valve, a frame enclosing the tubular layer and an elongate element coupled to the frame for allowing the tubular layer and frame to expand. For example, the frame may be biased to expand and withdrawal of the elongate element from openings in the frame can release the frame to expand into a larger diameter. Another embodiment includes a helical wire wrapped around the capsule for easy delivery through bends and a second helical wire that is advanced between windings of the first helical wire to selectively stiffen the capsule for withdrawal. Other embodiments include sock-like capsules that can be crumpled into shorter lengths by pulling a pull line attached to the capsule.

6 Claims, 14 Drawing Sheets

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,540,782 B1 | 4/2003 | Snyders |
| 6,569,196 B1 | 5/2003 | Vesely et al. |
| 6,575,959 B1 | 6/2003 | Sarge et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,579,381 B2 | 8/2009 | Dove |
| 7,585,321 B2 | 9/2009 | Cribier |

(56) References Cited

U.S. PATENT DOCUMENTS

| | | |
|---|---|---|
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,892,281 B2 | 2/2011 | Seguin et al. |
| 7,914,575 B2 | 3/2011 | Guyenot et al. |
| 7,993,394 B2 | 8/2011 | Hariton et al. |
| 8,007,992 B2 | 8/2011 | Tian et al. |
| 8,029,556 B2 | 10/2011 | Rowe |
| 8,092,521 B2 | 1/2012 | Figulla et al. |
| 8,118,866 B2 | 2/2012 | Herrmann et al. |
| 8,167,932 B2 | 5/2012 | Bourang |
| 8,206,437 B2 | 6/2012 | Bonhoeffer et al. |
| 8,216,174 B2 | 7/2012 | Wilk et al. |
| 8,317,858 B2 | 11/2012 | Straubinger et al. |
| 8,398,704 B2 | 3/2013 | Straubinger et al. |
| 8,416,643 B2 | 4/2013 | Magee |
| 8,449,599 B2 | 5/2013 | Chau et al. |
| 8,460,370 B2 | 6/2013 | Zakay |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0092858 A1 | 5/2004 | Wilson et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0137688 A1 | 6/2005 | Salahieh et al. |
| 2005/0137698 A1 | 6/2005 | Salahieh et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0025857 A1 | 2/2006 | Bergheim et al. |
| 2006/0058872 A1 | 3/2006 | Salahieh et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0195134 A1 | 8/2006 | Crittenden |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2007/0005131 A1 | 1/2007 | Taylor |
| 2007/0010877 A1 | 1/2007 | Salahieh et al. |
| 2007/0027534 A1 | 2/2007 | Bergeim et al. |
| 2007/0043435 A1 | 2/2007 | Seguin et al. |
| 2007/0066863 A1 | 3/2007 | Rafiee et al. |
| 2007/0088431 A1 | 4/2007 | Bourang et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0270943 A1 | 11/2007 | Solem |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082166 A1 | 4/2008 | Styrc et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0048656 A1 | 2/2009 | Wen |
| 2009/0054723 A1* | 2/2009 | Khairkhahan ..... A61B 17/0057 600/16 |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0099554 A1* | 4/2009 | Forster .................. A61F 2/2427 606/1 |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0004740 A1 | 1/2010 | Seguin et al. |
| 2010/0016958 A1 | 1/2010 | St. Goar et al. |
| 2010/0049313 A1 | 2/2010 | Alon et al. |
| 2010/0069852 A1 | 3/2010 | Kelley |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0238159 A1 | 9/2011 | Guyenot et al. |
| 2011/0264198 A1 | 10/2011 | Murray, III et al. |
| 2011/0288634 A1 | 11/2011 | Tuval et al. |
| 2011/0319989 A1 | 12/2011 | Lane et al. |
| 2012/0035722 A1 | 2/2012 | Tuval |
| 2012/0046741 A1 | 2/2012 | Tuval et al. |
| 2012/0046742 A1 | 2/2012 | Tuval et al. |
| 2012/0101570 A1 | 4/2012 | Tuval et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0283823 A1 | 11/2012 | Bonhoeffer et al. |
| 2012/0296418 A1 | 11/2012 | Bonyuet et al. |
| 2012/0310336 A1 | 12/2012 | Figulla et al. |
| 2013/0018458 A1 | 1/2013 | Yohanan et al. |
| 2013/0073035 A1 | 3/2013 | Tuval et al. |
| 2013/0079869 A1 | 3/2013 | Straubinger et al. |
| 2013/0190862 A1 | 7/2013 | Pintor et al. |
| 2013/0197622 A1 | 8/2013 | Mitra et al. |
| 2013/0310928 A1 | 11/2013 | Morriss et al. |
| 2014/0005767 A1 | 1/2014 | Glazier et al. |
| 2014/0316518 A1 | 10/2014 | Kheradvar et al. |
| 2015/0112430 A1 | 4/2015 | Creaven et al. |

(56) References Cited

U.S. PATENT DOCUMENTS

| | | |
|---|---|---|
| 2015/0297346 A1 | 10/2015 | Duffy et al. |
| 2015/0305866 A1* | 10/2015 | Dorn .................. A61F 2/95 623/1.11 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1469797 A1 | 10/2004 |
| EP | 1570809 A1 | 9/2005 |
| EP | 1653888 A2 | 5/2006 |
| EP | 1849440 A1 | 10/2007 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 91/17720 A1 | 11/1991 |
| WO | 92/17118 A1 | 10/1992 |
| WO | 93/001768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 01/28459 A1 | 4/2001 |
| WO | 01/35878 A2 | 5/2001 |
| WO | 01/49213 A2 | 7/2001 |
| WO | 01/54624 A1 | 8/2001 |
| WO | 01/54625 A1 | 8/2001 |
| WO | 01/62189 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 05/034812 | 4/2005 |
| WO | 2005/087140 A1 | 9/2005 |
| WO | 05/102015 | 11/2005 |
| WO | 2006/014233 A2 | 2/2006 |
| WO | 2006/034008 A2 | 3/2006 |
| WO | 06/108090 | 10/2006 |
| WO | 06/111391 | 10/2006 |
| WO | 2006/138173 A2 | 12/2006 |
| WO | 2008/005405 A2 | 1/2008 |
| WO | 2008/035337 A2 | 3/2008 |
| WO | 2008097590 A1 | 8/2008 |
| WO | 2008/147964 A1 | 12/2008 |
| WO | 2008/150529 A1 | 12/2008 |
| WO | 09/024859 | 2/2009 |
| WO | 2009091509 A1 | 7/2009 |
| WO | 09/116041 | 9/2009 |
| WO | 2010121076 A2 | 10/2010 |
| WO | 2011008812 A2 | 1/2011 |
| WO | 2011035327 A1 | 3/2011 |
| WO | 2011081997 A1 | 7/2011 |
| WO | 2011130093 A1 | 10/2011 |
| WO | 2012/095455 A2 | 7/2012 |

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 104-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Transluminal Placement of Endovascular Stent-Grafts for the Treatment of Descending Thoracic Aortic Aneurysms, New Engl. J.Med., 1994; 331:1729 34.

Dotter, M.D., Charles T., "Transluminal Treatment of Arteriosclerotic Obstruction," University of Oregon's Minthom Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, http://www.nytimes.com/1991/01/03/health/device-that-opens-clogged-arteries-gets-a-jfaili . . . , Jul. 29, 2009, 2 pages.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschluß des Ductus Arteriosus Persistens ohne Thorakotomie," Thoraxchirurgie Vaskuläre Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Intery Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

(56) References Cited

OTHER PUBLICATIONS

Serruys, P.W., et al., "Stenting of Coronary Arteries. Are we the Sorcerer's Apprentice?," European Heart Journal (1989)10, 774-782, pp. 37-45, Jun. 13, 1989.
Sigwart, Ulrich, "An Overview of Intravascular Stents: Old and New," Chapter 48, Textbook of Interventional cardiology, 2nd Edition, W.B. Saunders Company, Philadelphia, PA, © 1994, 1990, pp. 803-815.
Uchida, Barry T., et al., "Modifications of Gianturco Expandable Wire Stents," AJR:150, May 1988, Dec. 3, 1987, pp. 1185-1187.
Urban, M.D., Philip, "Coronary Artery Stenting," Editions Médecine et Hygiène, Genève, 1991, pp. 5-47.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Wheatley, M.D., David J., "Valve Prostheses," Rob & Smith's Operative Surgery, Fourth Edition, pp. 415-424, Butterworths 1986.
EP Search Report dated Jan. 28, 2016 for EP15181583.
EP Search Report dated Feb. 23, 2016 for EP15197122.

\* cited by examiner

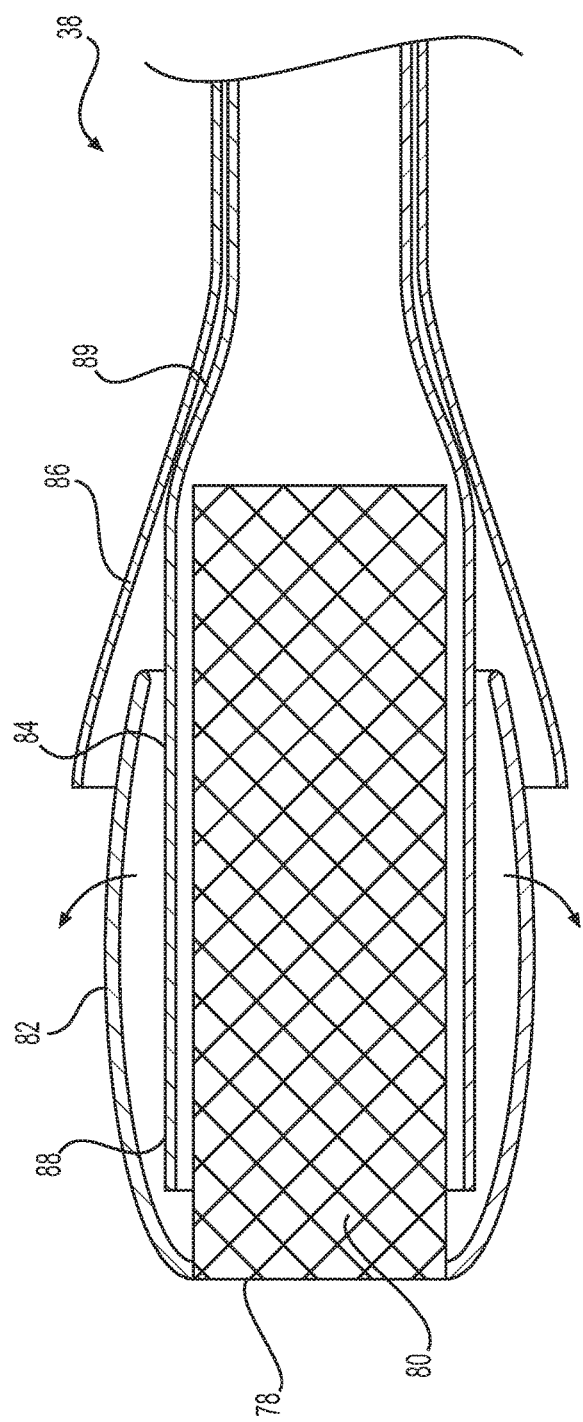
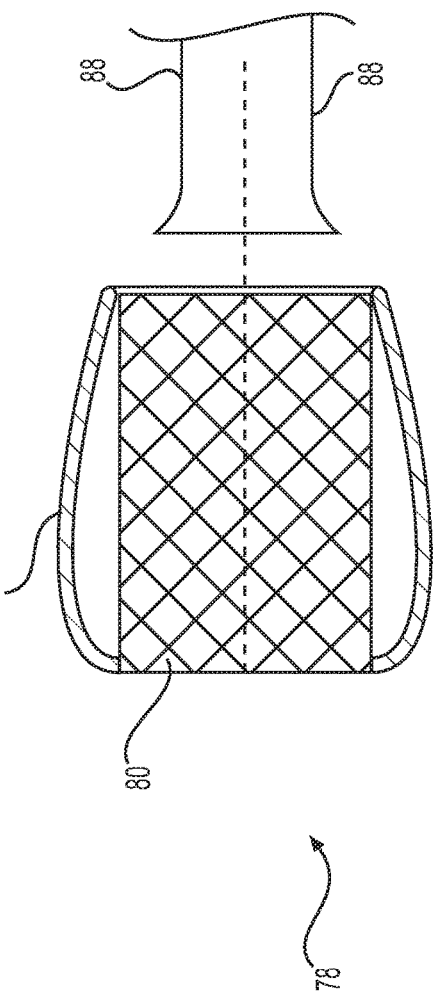
FIG. 17
FIG. 18

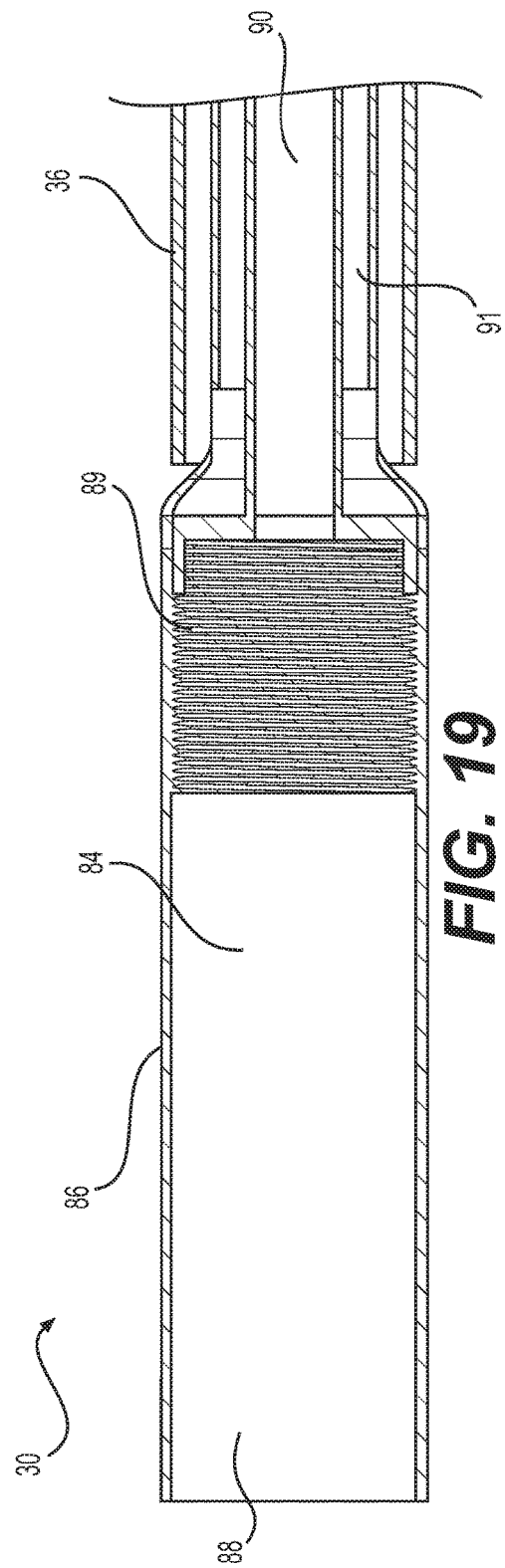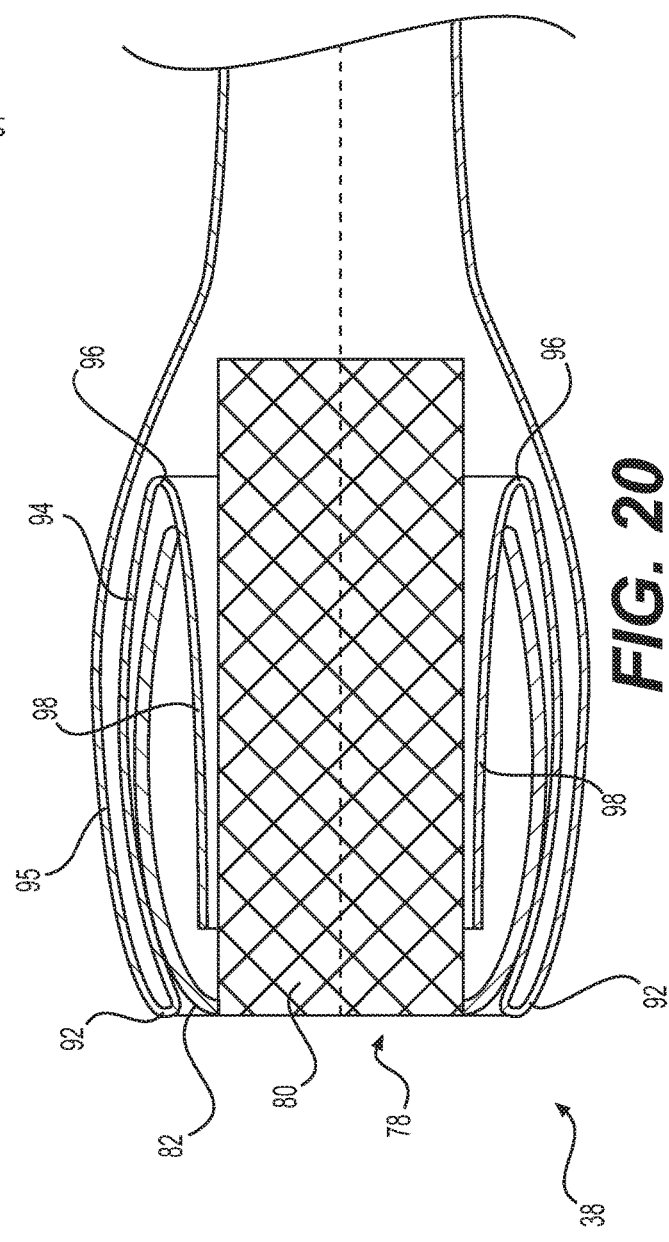

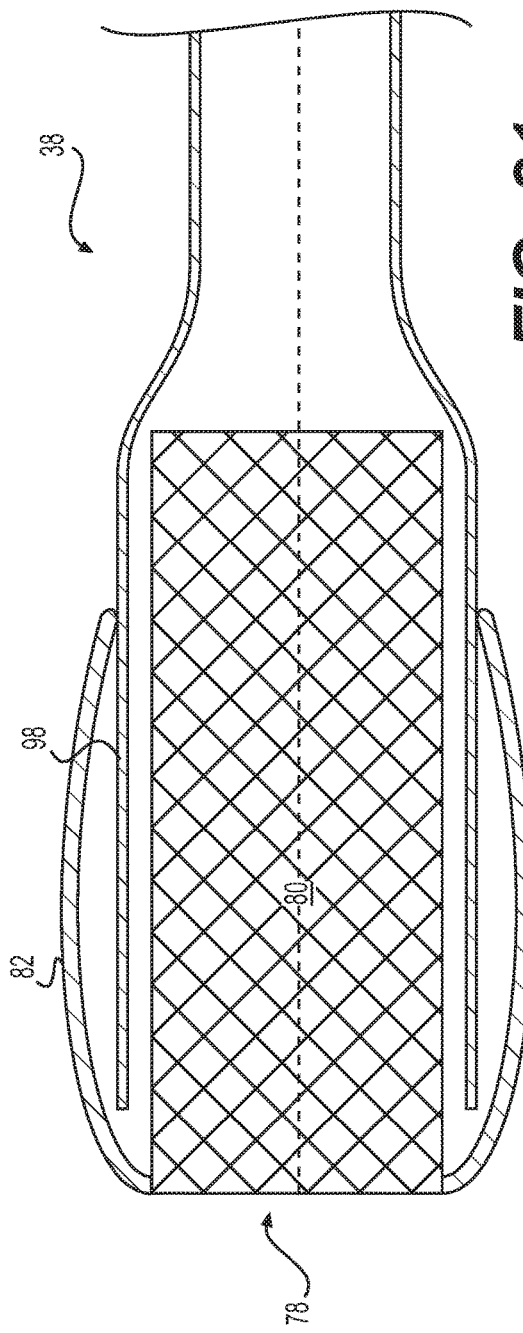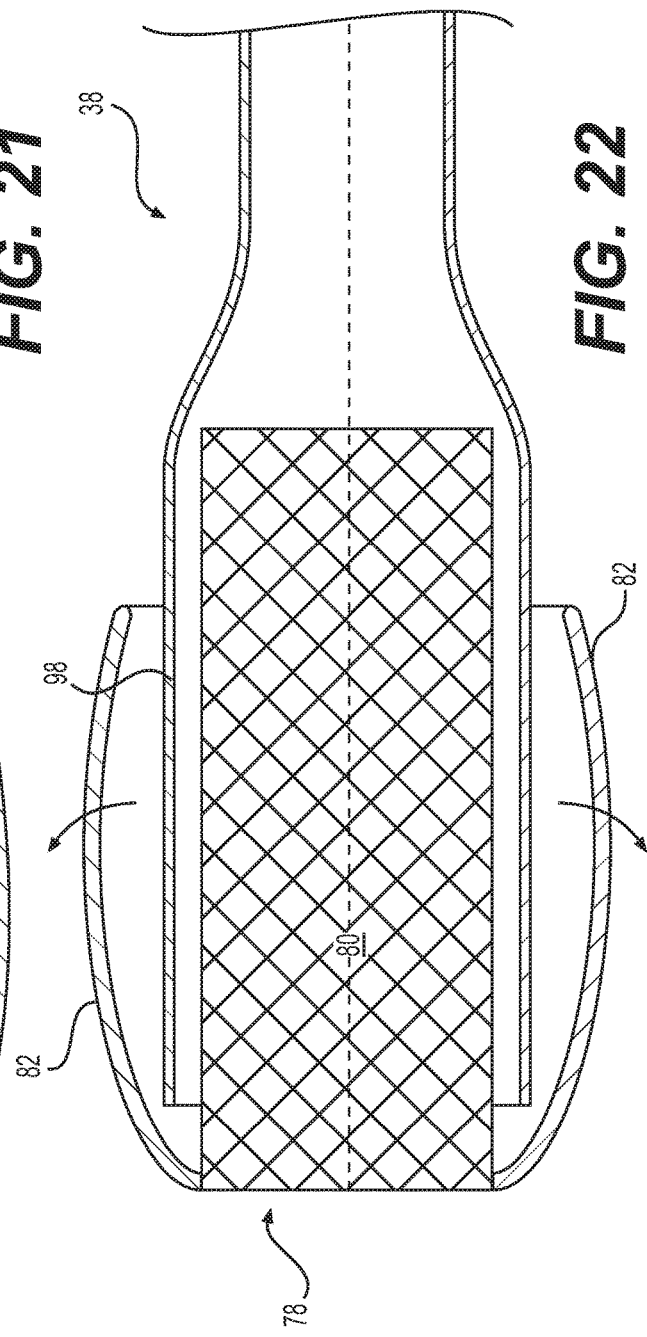

IMPLANT DELIVERY CAPSULE

RELATED APPLICATIONS

This application claims the benefit of U.S. Provisional Application No. 62/253,464, filed Nov. 10, 2015, which is hereby incorporated in its entirety.

FIELD

The present application concerns embodiments of a capsule for delivering a prosthetic device, and in particular capsules for delivery of prosthetic heart valves.

BACKGROUND

Endovascular delivery catheter assemblies are used to implant prosthetic devices, such as prosthetic heart valves, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature. An introducer sheath generally has an elongated sleeve that is inserted into the patient's vasculature and a housing with one or more sealing valves that allows a delivery apparatus to be placed in fluid communication with the vasculature while preventing blood loss. A conventional introducer sheath typically requires a tubular loader to be inserted through the seals in the housing to provide an unobstructed path through the housing, thereby allowing a prosthetic device to be passed through the introducer sheath.

Certain approaches through the heart for mitral valve replacement can be particularly challenging for delivery of prosthetic mitral valves due to the sharp turns needed near the end of the introducer sheath. An example of a stent-mounted mitral valve prosthetic is described in U.S. Pat. No. 8,449,599, which is hereby incorporated herein by reference. FIG. 67 of the '599 patent (replicated herein as FIG. 1) illustrates delivery of a prosthetic mitral valve via a transseptal approach. More specifically, an incision is made in the atrial portion of a septum 30 for allowing access from a right atrium 26 to a left atrium 4. A sheath 2102 of a delivery catheter 2100 is inserted into the left atrium 4 and bent sharply in the direction of the mitral valve. Once in the left atrium 4, the distal end of the sheath 2102 is moved across the mitral annulus such that ventricular anchors 126 of the prosthetic valve 100 are positioned beyond the mitral leaflets 10, 12. The prosthetic valve is expelled from the distal end of the sheath 2102 using pusher shaft 2106.

Despite the improvements provided by the '599 patent, the sharp bend in the introducer sheath (prior to reaching the mitral valve) increases the difficulty of withdrawing the sheath relative to the pusher and mitral valve. The sheath has to be retracted backwards around two bends. Also, there is limited space in the heart chambers (left ventricle and left atrium) for relative movement of the introducer sheath and the deploying prosthetic mitral valve. The lack of space makes it difficult for the cardiologist to deliver the prosthetic mitral valve. Thus, there remains a need for improvements to delivery systems for prosthetic mitral valves, especially for transseptal approaches.

SUMMARY

Disclosed herein are embodiments of delivery capsules used for delivering prosthetic implants around the relatively tight bends of a catheter. In particular, disclosed herein are delivery capsules including a tubular layer for holding the heart valve and a frame that is held in a curled configuration by an elongate element. Withdrawal of the elongate element releases the frame to expand into a larger diameter. Another embodiment includes a helical wire wrapped around the capsule for easy delivery through bends and a second helical wire that is advanced between windings of the first helical wire to selectively stiffen the capsule for withdrawal. Other embodiments include sock-like capsules that can be crumpled into shorter lengths by pulling a pull line attached to the capsule.

In the embodiments disclosed herein, a delivery system extends through the vasculature to access a native heart valve. The delivery systems include a catheter configured to extend through the vasculature. The catheter has a distal end for positioning in proximity to the native heart valve. The delivery systems also include an expandable prosthetic heart valve coupled to the distal end of the catheter for placement within the native heart valve.

Some embodiments of the delivery system disclosed herein include a tubular layer defining a lumen for containing the prosthetic heart valve, a frame coupled to the tubular layer and encircling the tubular layer, and a thin, elongate element extending through the frame. In some embodiments, the frame is comprised of a stiff fabric. The elongate element holds the frame in an inwardly curled configuration and against an outward bias of the frame. The inwardly curled configuration narrows the lumen and holds the tubular layer and prosthetic heart valve in a crimped configuration. The elongate element is further removable from the frame to release the tubular layer and frame into an expanded configuration. In some embodiments, the thin elongate element is a rod extending through a lumen defined by the catheter.

The frame can include a plurality of fingers, each of the fingers defining an opening. A first set of the fingers can extend in a clockwise direction and a second set of the fingers can extend in a counter-clockwise direction. The elongate element extends through the opening of each of the fingers to hold the frame in the inwardly curled configuration. The first set of fingers and second set of fingers can be engaged to axially align the openings with the elongate element passing therethrough in the inwardly curled configuration, and then disengaged with sliding removal of the elongate element. This disengagement causes the frame to assume the expanded configuration.

The frame can also include a base sheet. The first set of fingers extends from a first longitudinal edge of the base sheet and the second set of fingers extends from a second longitudinal edge of the base sheet opposite the first longitudinal edge. In some implementations, each of the fingers has a free end defining the opening, and the free end may include a loop defining the opening.

In some implementations, the frame and tubular layer are configured to remain with the expandable prosthetic valve upon removal of the catheter. The prosthetic valve can include a plurality of tissue leaflets secured to the tubular layer and frame.

In some implementations, the frame includes a helical wire helically extending along the tubular layer. The helical wire may define a loop at one end. The elongate element engages the loop and applies tension to the helical wire to hold the helical wire in the inwardly curled configuration. The elongate element may be, for example, a suture extending through a lumen of the catheter.

Other embodiments of the delivery system disclosed herein include a flexible capsule defining a lumen. The capsule is configured to contain the prosthetic heart valve. It includes a tubular layer and a capsule helical wire attached to and encircling the tubular layer. In some implementations, the tubular layer includes a thin polymer encapsulating the capsule helical wire. An inside surface of the tubular layer can, in some examples, be smooth. The capsule helical wire has a helical pitch space defined between adjacent windings of the capsule helical wire. In some implementations, the helical pitch space is defined on an outside surface of the tubular layer.

The delivery systems of this embodiment also include a torque shaft having a proximal end and a distal end and a proximal helical wire coupled to the distal end of the torque shaft. The proximal helical wire has a diameter and pitch matching the helical pitch space. Rotation of the proximal end of the torque shaft rotates the proximal helical wire and axially advances the proximal helical wire into the pitch space of the capsule helical wire so as to stiffen the capsule for retrieval of the prosthetic heart valve into the lumen.

The delivery systems of this embodiment can also include a delivery sheath having a lumen containing the proximal end of the catheter. The capsule helical wire can be configured to reduce in diameter for withdrawal of the flexible capsule into the lumen of the delivery sheath. An elongate puller can be coupled to a distal end of the flexible capsule and configured to pull the proximal end of the flexible capsule to reduce the helical pitch space and reveal the prosthetic heart valve.

Other embodiments of the delivery system disclosed herein can include a delivery sheath. The delivery sheath is configured to extend through the vasculature, and has a proximal end and a distal end (the distal end for positioning in proximity to the native heart valve). The delivery sheath defines a lumen, and the catheter extends through the lumen of the delivery sheath. Also included is a tubular capsule for containing the expandable prosthetic heart valve. The tubular capsule includes a flexible wall material (such as a woven material) defining a lumen, a proximal end, and a distal end. A pull line extending through the lumen of the delivery sheath is attached to one of the ends (proximal or distal) of the tubular capsule, and configured to pull on the tubular capsule. The flexible wall material is configured to crumple in response to pulling by the pull line to reveal the expandable prosthetic heart valve. The delivery systems of this embodiment may further include a nose positioned distal to the tubular capsule. The pull line can extend through the nose and doubles back to attach to the proximal end of the tubular capsule to pull the proximal end of the tubular capsule distally.

Other embodiments of the delivery system disclosed herein can include an expandable prosthetic valve having a cylindrical frame and at least one paddle, and a tubular capsule with a proximal end and a distal end. The tubular capsule includes a flexible wall material having an inner layer extending around the cylindrical frame and an outer layer extending around the paddle. A pulling element is attached to the proximal end of the tubular capsule and extends proximally along the catheter. Pulling proximally on the tubular capsule using the pulling element first releases the paddle and then releases the cylindrical frame.

For the delivery systems of this embodiment, the inner layer can have a length greater than the outer layer. The inner layer can also have a crumple zone configured to be taken up without movement of a distal end of the inner layer while the outer layer releases the paddle. The distal end of the inner layer may moves once the crumple zone is taken up to release the cylindrical frame. In some implementations, the inner layer has a free end and the outer layer has a free end. In some implementations, the tubular capsule extends distally to a distal bend and extends proximally from the distal bend to define the outer layer to a proximal bend then extends distally from the proximal bend under the paddle and over the cylindrical frame to define the inner layer.

DESCRIPTION OF DRAWINGS

FIG. 17 is a partial sectional view of the capsule of FIG. 16 with a first outer layer withdrawn to allow actuation of the paddles of the prosthetic mitral valve;

FIG. 18 is a partial sectional view of a second inner layer of the capsule of FIG. 16 withdrawn and the prosthetic mitral valve in an expanded configuration;

FIG. 19 is a partial sectional view of a multi-layer capsule of another embodiment of the present invention;

FIG. 20 is a partial sectional view of a sock-like capsule of another embodiment of the present invention having bends for holding a mitral valve with paddles in a crimped configuration;

FIGS. 21 and 22 are partial sectional views of the capsule in FIG. 20 partially withdrawn to remove the bends and free the paddles for expansion;

DETAILED DESCRIPTION

Figure 1:
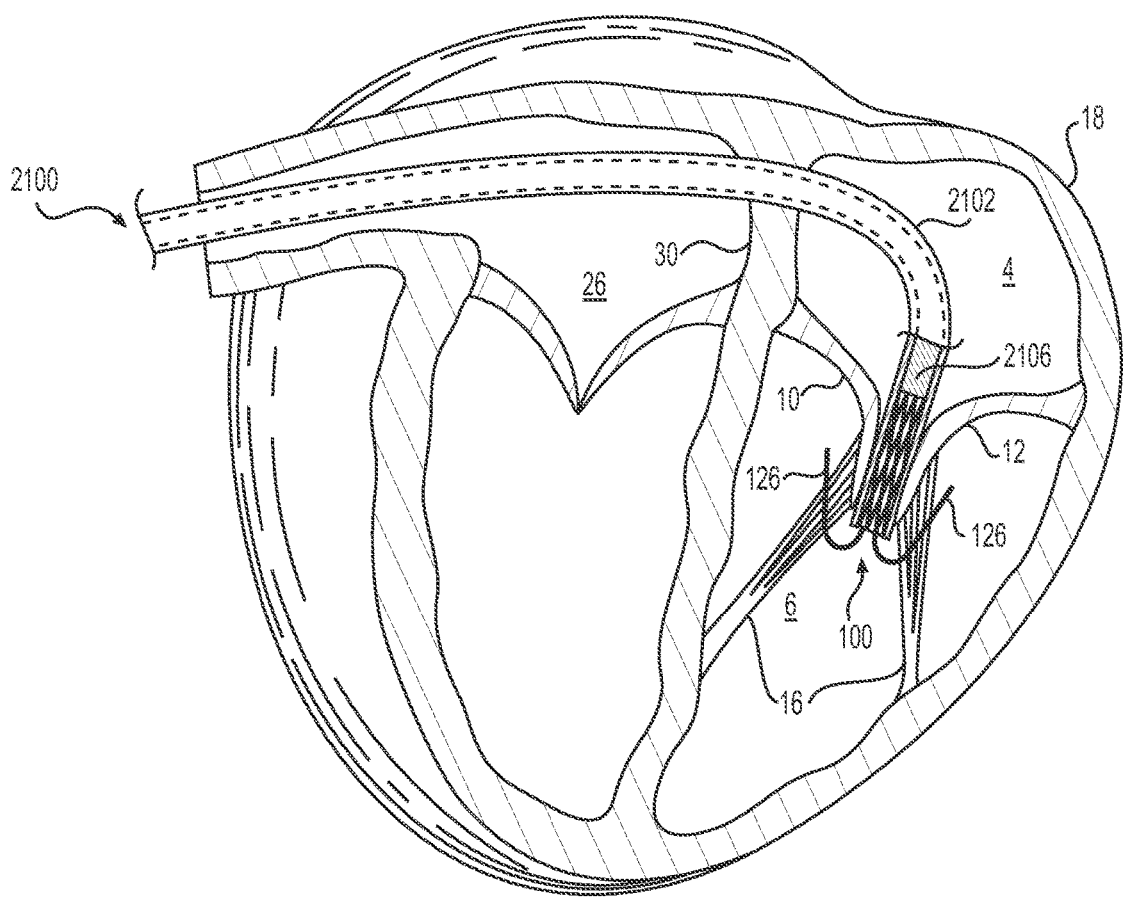
FIG. 1 is a sectional view of a heart with a delivery system delivering a prosthetic valve into a native mitral valve.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed herein are embodiments of delivery capsules for delivering prosthetic implants around the relatively tight bends of a catheter. In particular, disclosed herein are delivery capsules including a tubular layer for holding the heart valve and a frame that is held in a curled configuration by an elongate element, such as a suture, a rod, or a wire. Withdrawal of the elongate element releases the frame to expand into a larger diameter. Another embodiment includes a helical wire wrapped around the capsule for easy delivery through bends and a second helical wire that is advanced between windings of the first helical wire to selectively stiffen the capsule for withdrawal. Other embodiments include sock-like capsules that can be crumpled into shorter lengths by pulling a pull line attached to the capsule.

The capsules disclosed herein may also be used to deliver various types of implantable devices, such as self-expanding implantable heart valves, stents or filters. The terms "implant" and "implantable" as used herein are broadly defined to mean anything—prosthetic or not—that is delivered to a site within a body. A diagnostic device, for example, may be an implantable. The term "implant" as used herein also does not need to be a permanent implant—for example a balloon is an implant temporarily—but could be any device delivered into the body for a procedure. The disclosed capsules are, however, well adapted for use with self-expanding prosthetic heart valves and in particular prosthetic heart valves delivered into particularly tight spaces or through tortuous pathways.

Figure 2:
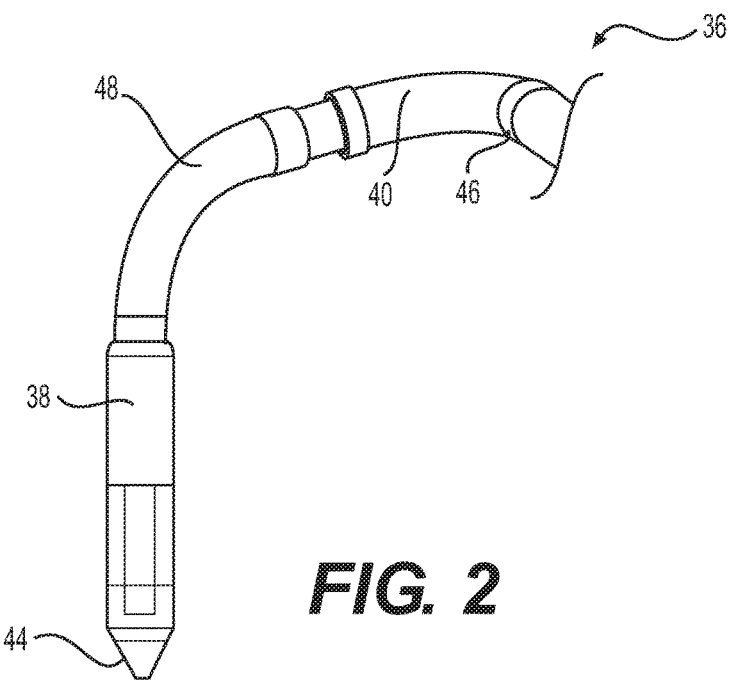
FIG. 2 is a plan view of a distal end of a mitral valve delivery system.

FIG. 2 shows a distal end of a delivery catheter 36 generally having a tubular structure and including a capsule 38 and a nosecone 44. The delivery catheter 36 includes a first bend 46 and a second bend 48 before reaching the distally positioned capsule 38. The first bend 46 can be due to a steering component bending a normally straight portion of the tubular structure or pre-bent, biased portion of the tubular structure assuming its natural shape. The second bend 48 similarly may be bent by steering, or assuming a pre-bent shape. For example, the portion defining the second bend 48 may be extended out of the more proximal portion of the tubular structure defining the first bend 46 and then, under bias of a pre-bent wall structure, may assume the bent shape. Regardless, the bends 46, 48 illustrate one of many configurations in which embodiments of the present invention are advantageous—tight or confined spaces where delivery/retrieval occurs proximate a bend in the catheter or other delivery device.

The capsule 38 shown in FIG. 2 generally represents any of the capsule embodiments disclosed herein. The capsule is configured to mate with the nosecone 44 to define a receptacle for delivery of an implant, such as a self-expanding prosthetic heart valve in a crimped configuration. The capsule 38 can be delivered by pushing an inner catheter tubular structure—such as the one defining the second bend 48—out of a delivery sheath or other tubular structure—such as the one defining the first bend 46 in FIG. 2. Once the capsule 38 is free, generally, the capsule needs to be somehow retracted, removed or disengaged from its position covering and/or restraining the implant. Various embodiments disclosed herein below facilitate retraction or removal or disengagement without requiring a large space and/or with a proximate sharp bend in the tubular structure of the delivery catheter 36.

Figure 3:
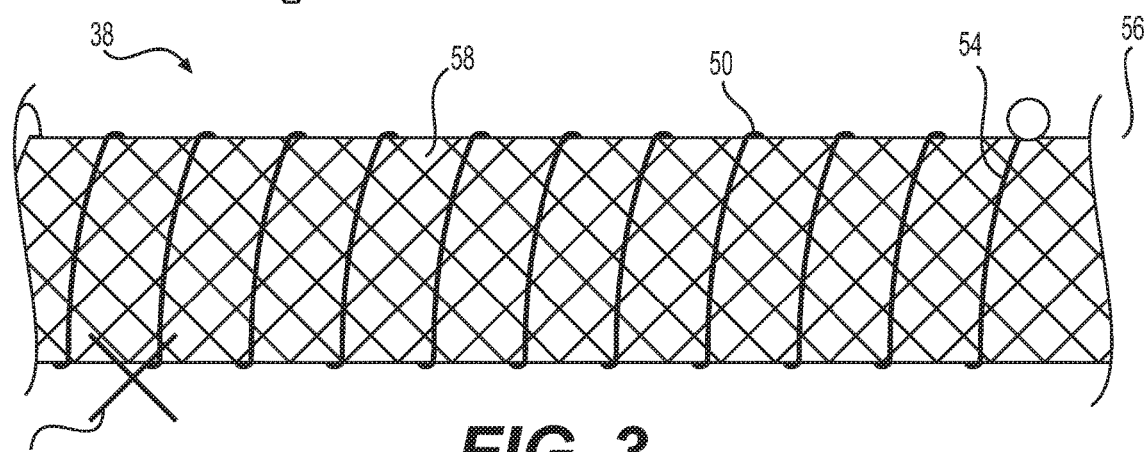
FIG. 3 is a schematic of a capsule of one embodiment of the present invention including a helical thread wound around a prosthetic valve frame.

FIG. 3 shows one embodiment of a capsule 38 formed of a helical suture or wire frame 50 wrapped around a sheath or, in the illustrated case, a valve frame 58 containing a tissue valve (e.g., made from pericardium). The helical wire frame 50 is comprised of a wire that is fixed at a distal end 52 to a distal portion of the valve frame 58 and wraps around the outside of the valve frame. The helical wire frame 50 also includes a proximal end 54 having defined thereon a loop or other feature that facilitates attachment of a suture 56 or other elongate member. Deployment is achieved by releasing tension in the helical wire frame 50 and detaching the suture 56 from the wire frame. The release of tension allows the helical wire frame 50 to expand to an enlarged, biased shape. Or, the release of tension in the helical wire frame 50—if the wire frame is unbiased, such as by being comprised of suture—can allow a self-expanding valve frame 58 to expand into position within a native mitral valve annulus.

In a sense, the capsule 38 is partially formed by the valve frame 58, or the capsule could be regarded as being the helical wire frame 50 standing alone. The capsule could also be attached to a dedicated tubular cover that is part of the capsule 38. Of course, an advantage of having the capsule comprise the helical wire frame 50 standing alone is that the helical wire frame 50 can be left in place in the implant location. It does not have to be withdrawn into the second bend 48 of the delivery catheter 36. Only the suture 56 need be withdrawn and it easily pulls back into the delivery catheter 36, even around tight bends.

Figure 4:
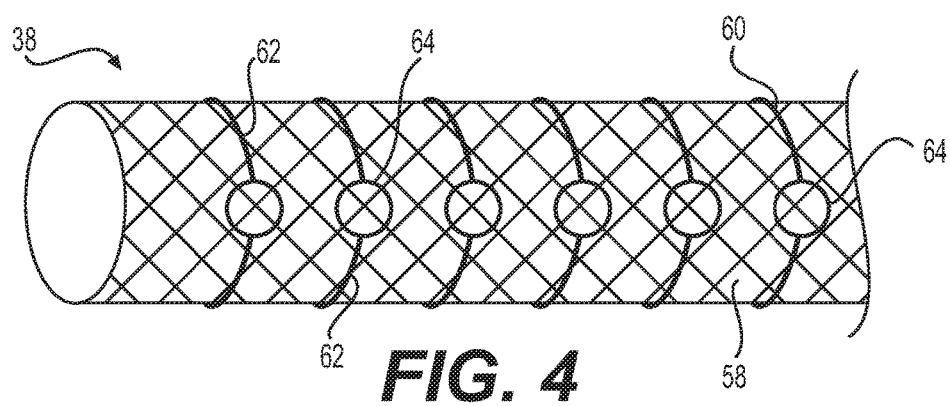
FIG. 4 is a schematic of a capsule of another embodiment of the present invention including fingers holding a prosthetic valve in a crimped configuration.
Figure 5:
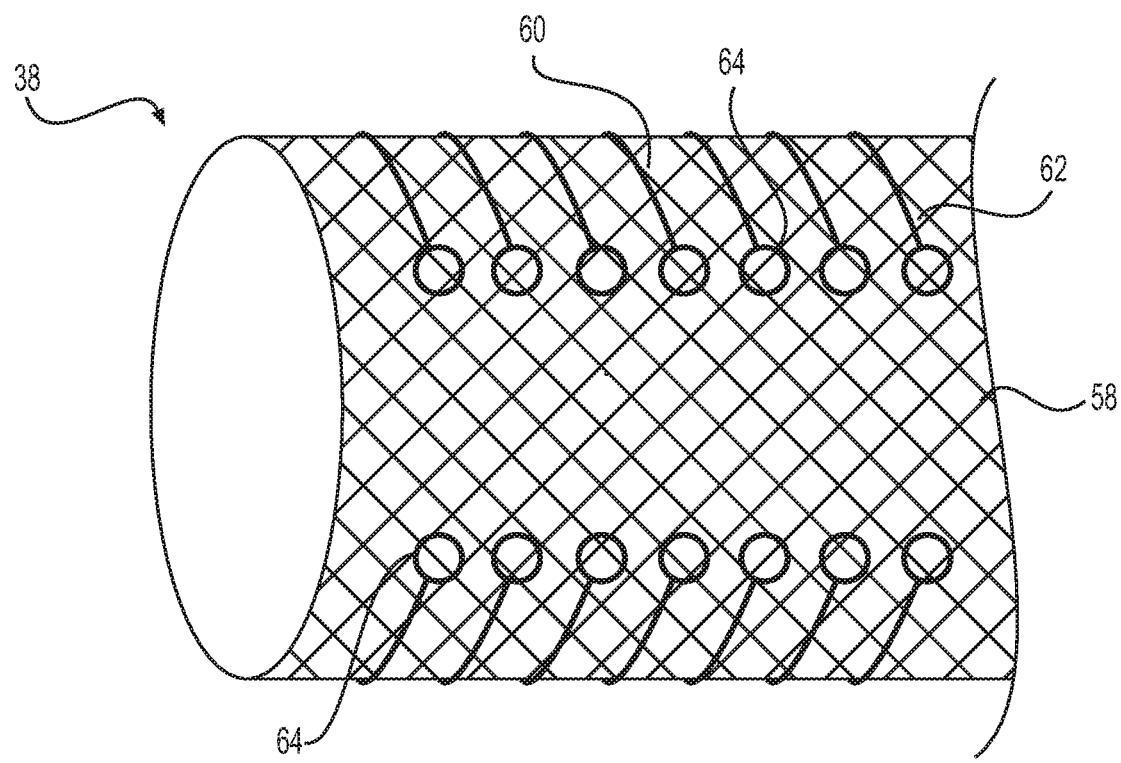
FIG. 5 is a schematic of the capsule and prosthetic valve of FIG. 4 in an expanded configuration.

FIGS. 4 and 5 show another embodiment, wherein the capsule 38 includes a differently configured wire capsule frame 60 including a plurality of fingers 62. The fingers 62 extend circumferentially around the valve frame 58 and have ends including loops 64. The fingers 62 thus have a C-shape with free ends having the loops 64. The fingers 62, in the embodiment of FIG. 4, are axially spaced along the outside of the valve frame 58. The loops 64 at the ends of the fingers are in overlapping, paired relationships on the outside surface of the valve frame 58. Also, the pairs of loops 64 are positioned in alignment extending in the axial direction of the valve frame 58. A suture or wire (not shown) can extend through the aligned pairs of loops to hold the fingers 62 in a smaller diameter or inwardly curled configuration in FIG. 4. Holding the fingers in the smaller diameter configuration also holds the valve frame 58 in a crimped condition for delivery.

FIG. 5 shows an expanded configuration of the valve frame 58, wherein the suture 56 has been removed from engagement of the overlapping pairs of loops 64. As each loop pair is disengaged, the bias of the fingers 62 and/or the valve frame 58 urges the valve frame into the expanded configuration. Like the embodiment of FIG. 3, withdrawal of just the suture 56 or other elongate element is relatively easy and the fingers 62 remain with—and contribute to—the valve frame 58.

Figure 6:
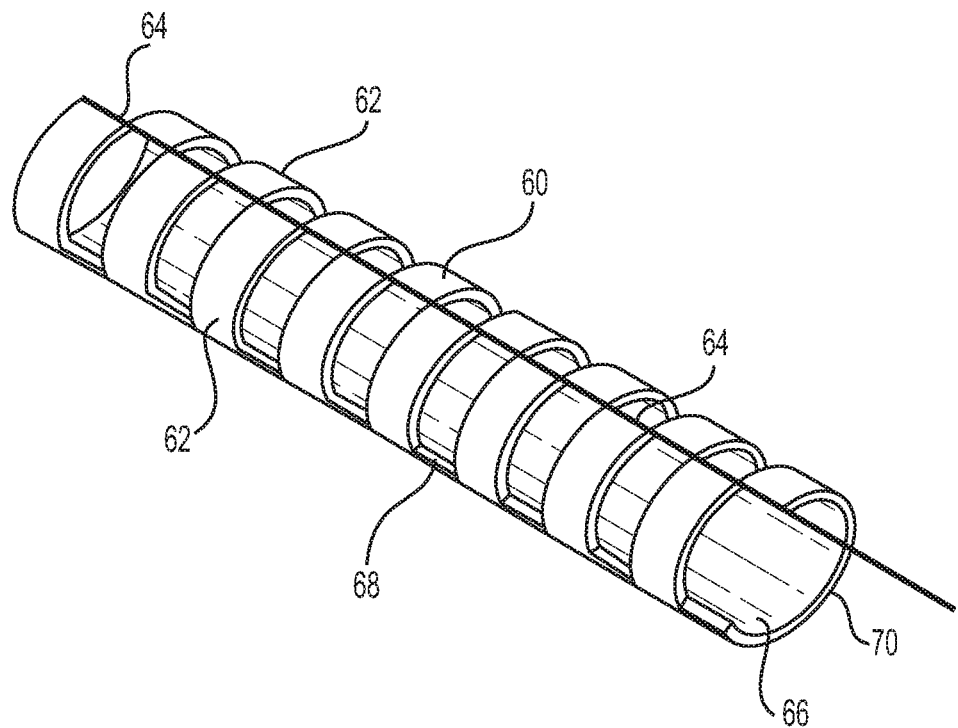
FIG. 6 is a perspective view of a capsule frame of another embodiment of the present invention including interdigitating fingers curled into a crimped configuration.
Figure 7:
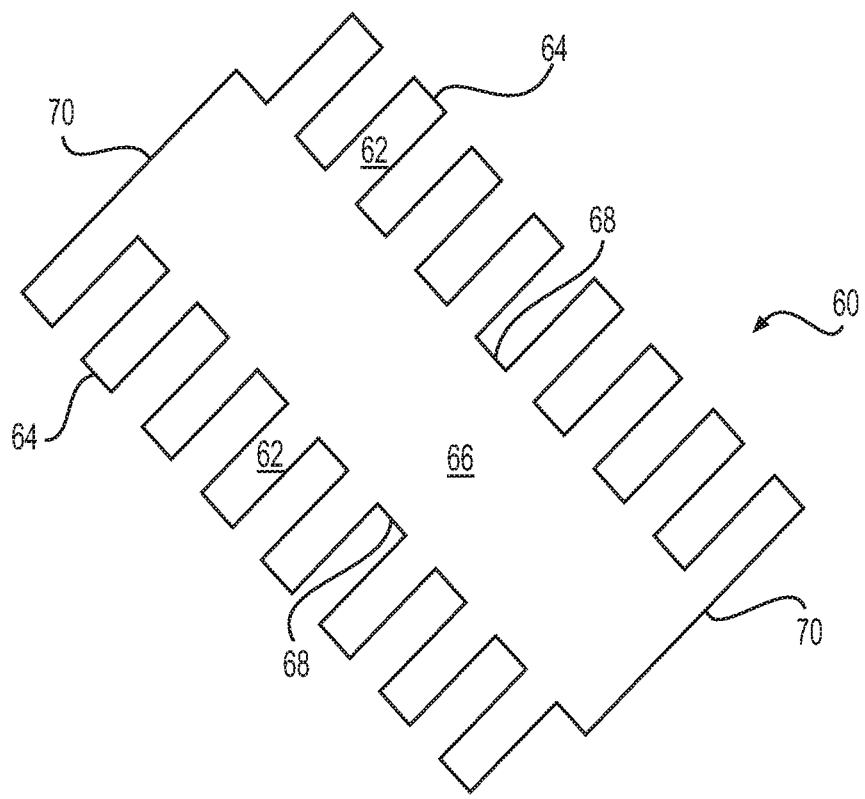
FIG. 7 is a plan view of the capsule frame shown in FIG. 6.
Figure 8:
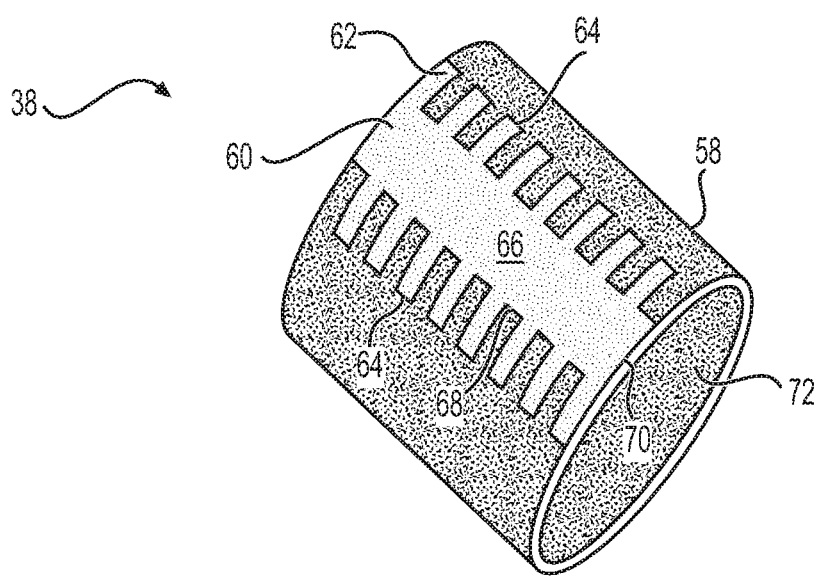
FIG. 8 is a perspective view of the capsule frame of FIG. 6 attached to a prosthetic valve frame body and in an expanded configuration.

FIGS. 6 through 8 illustrate yet another embodiment, wherein the frame 60 includes fingers 62 that extend in clockwise and counterclockwise directions (when viewed along the axis of the valve frame 58). The frame 60 also includes a base sheet 66 having a rectangular shape with a pair of longitudinal edges 68 and circumferential edges 70. The circumferential edges 70 extend between the longitudinal edges, as shown in FIG. 7. The fingers 62 extend from the longitudinal edges 68 and are spaced there along—with the fingers on one of the edges out of phase in their spacing with the fingers on the other one of the edges. Thus, when the base sheet 66 is rolled up into a tubular configuration, as shown in FIG. 6, the oppositely facing fingers extend between each other or "interdigitate." The dimensions of the fingers 62 relative to the base sheet may vary. For example, the capsule may have a narrow base sheet 66 and long fingers 62, or vice versa having a wide base sheet and short fingers.

Each of the fingers 62 includes a loop 64 at its free edge. Therefore, when the fingers are interdigitated, the loops are aligned on the outside surface of the valve frame 58. The suture 56, or other elongate member—such as a wire or rod—extends through the aligned loops to hold the frame 60 in the curled configuration shown in FIG. 6. FIG. 8 shows the valve frame 58 in the expanded configuration after withdrawal of the rod 56 from the aligned loops 64. After withdrawal of the rod, the base sheet 66 and fingers 62 expand toward their flat configuration, as shown in FIG. 7. Even in the expanded condition, the base sheet 66 and fingers 62 are not entirely flat and so continue to exert a bias urging the valve frame 58 to its largest diameter. This helps to seat and or maintain positioning of the valve frame 58 in the native mitral valve annulus, for example.

Figure 30:
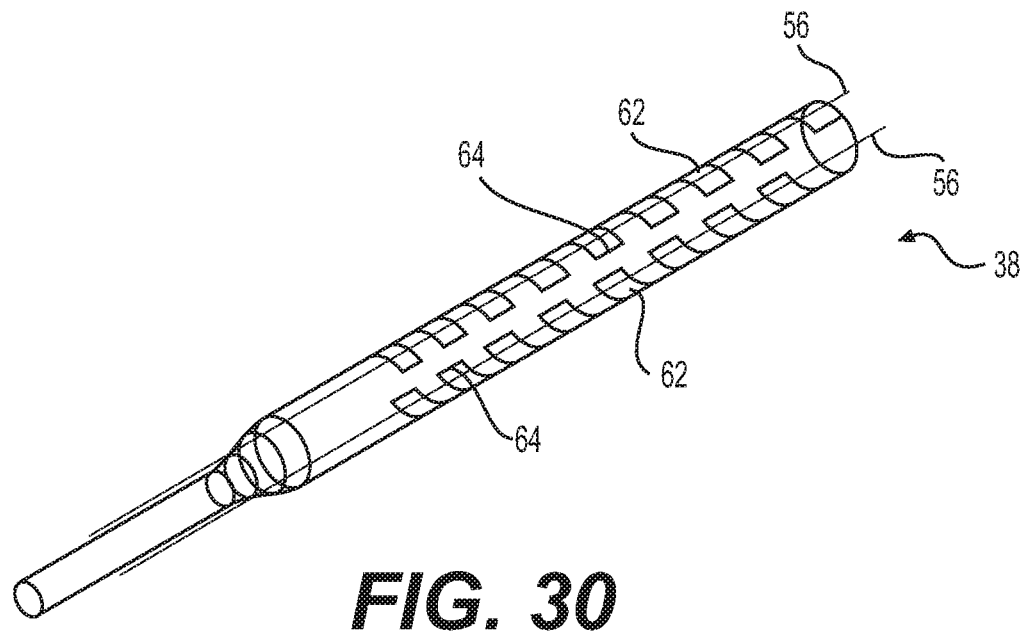
FIGS. 30-31 are perspective views of capsule frames of another embodiment of the present invention including multiple suture lines for staged deployment.
Figure 31:
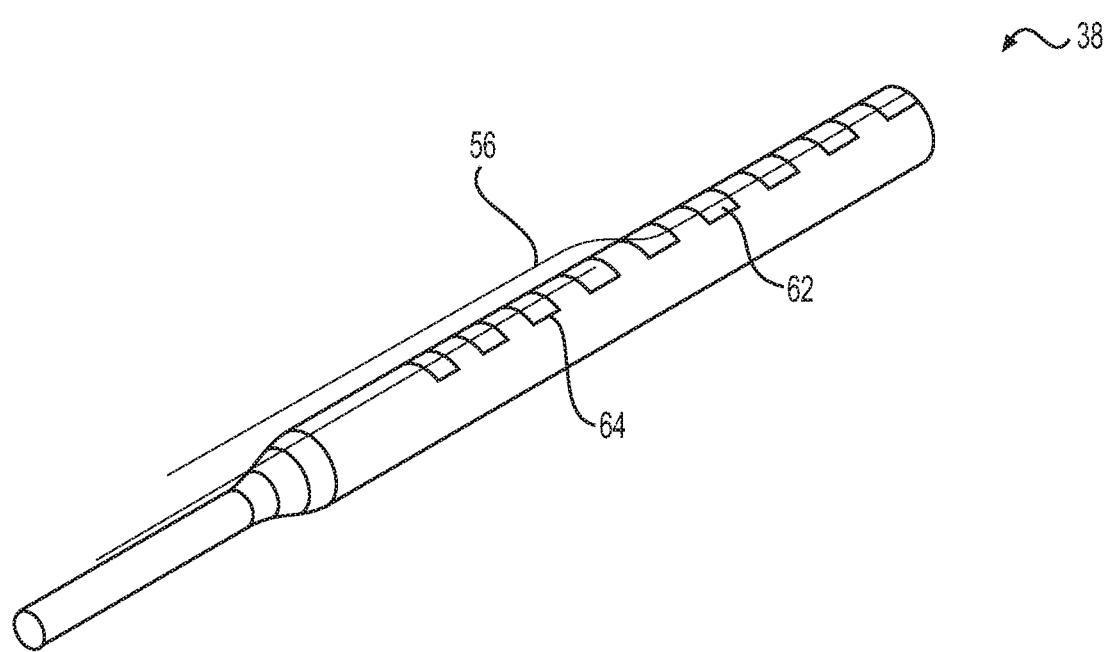

FIGS. 30 and 31 show embodiments of capsule 38 that include multiple frames 60 with fingers 62 terminating in loops 64 at their free edges. Two or more arrays positioned radially around the circumference of the capsule may be deployed separately by distinct sutures 56, allowing for a directionally defined and staged deployment. In FIG. 31, distinct sutures 56 are attached along separate lengths of the array of fingers 62 and loops 64. Staged release of the distinct sutures 56 enables staged control of deployment along the length of the capsule.

The frames 50, 60 (and other features described herein benefiting from elastic memory) can be constructed of materials with some stiffness and elasticity. For example, the frames could be constructed of a super elastic nitinol which is capable of higher elastic strains that can be present in the curled configurations (when the valve is in a crimped condition). At the same time, the elasticity of the nitinol allows it to expand back into its memory shape, such as the flat configuration or the larger diameter C-shapes shown in the figures. Other materials could also be used such as more pliable polymers, depending, for example, upon the desired amount of elastic bias contributed by the capsule frames versus the valve frame 58. Polymers may include nylon, polyethylene terephthalate (PET), expanded polytetrafluoroethylene (ePTFE), or ultra-high-molecular-weight-polyethylene based materials such as, for example, DYNEEMA fibers.

The valve frames can include circumferential fabric tubes—such as the tubes shown in FIGS. 5 and 8. The circumferential fabric tubes can be configured to block blood flow around the valves or other valve frame components (such as stents). The fabric tubes also do not substantially resist expansion of the capsule or valve frames once released by withdrawal of the suture 56. Advantageously, the capsule 38 can remain as part of the implanted valve and does not require withdrawal back through the delivery system. As a result, deployment can be performed with lower forces—retracting a capsule from over the valve frame (as in conventional systems) generates friction forces. The capsule can be a much larger diameter because it need not be withdrawn back through the delivery system.

FIGS. 9 through 13 illustrate an embodiment of capsule 38 including a tubular layer 72 and a capsule helical wire 74. The tubular layer 72 defines a lumen within which the self-expanding prosthetic heart valve can be restrained for delivery. The tubular layer can be constructed of materials, such as a PTFE material, elastomer, a semi-compliant polymer or woven materials, which are flexible and relatively impermeable to fluids.

Figure 9:
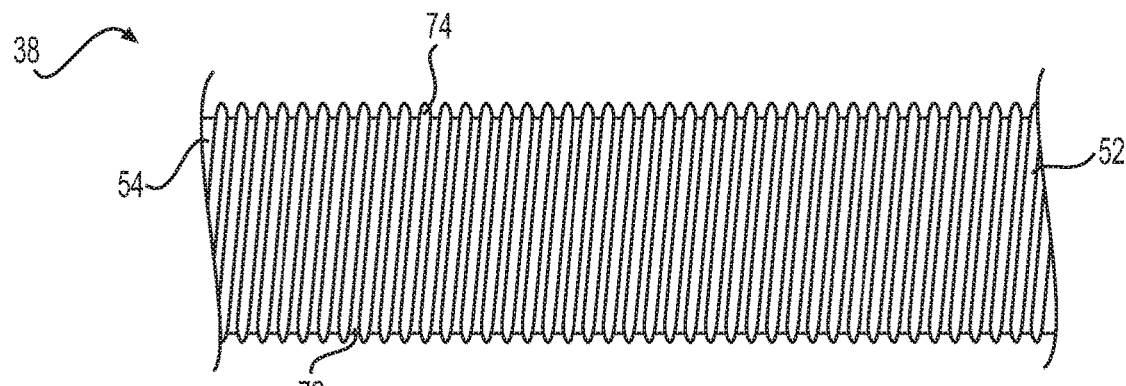
FIG. 9 is a side elevation view of another embodiment of a capsule including a helical spring frame.
Figure 10:
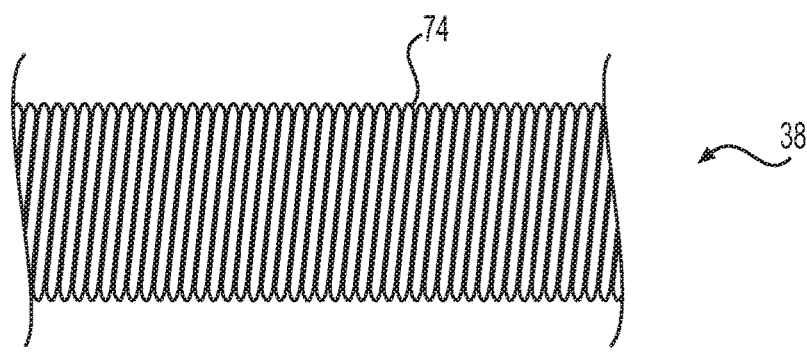
FIG. 10 is a side elevation view of the capsule of FIG. 9 in an axially compressed condition.

The capsule helical wire 74, as shown in FIG. 9, includes a flexible helical wire that is attached to and encircles the tubular layer 72. The capsule helical wire 74 has a helical pitch space defined between adjacent windings of the helical shape as it extends along the outside surface of the tubular layer. The capsule 38 with the helical wire can advantageously compress, as shown in FIG. 10, to reduce the helical pitch space to zero. This shortens and stiffens the capsule 38 for advancement against friction within the delivery sheath and/or body lumens.

Figure 11:
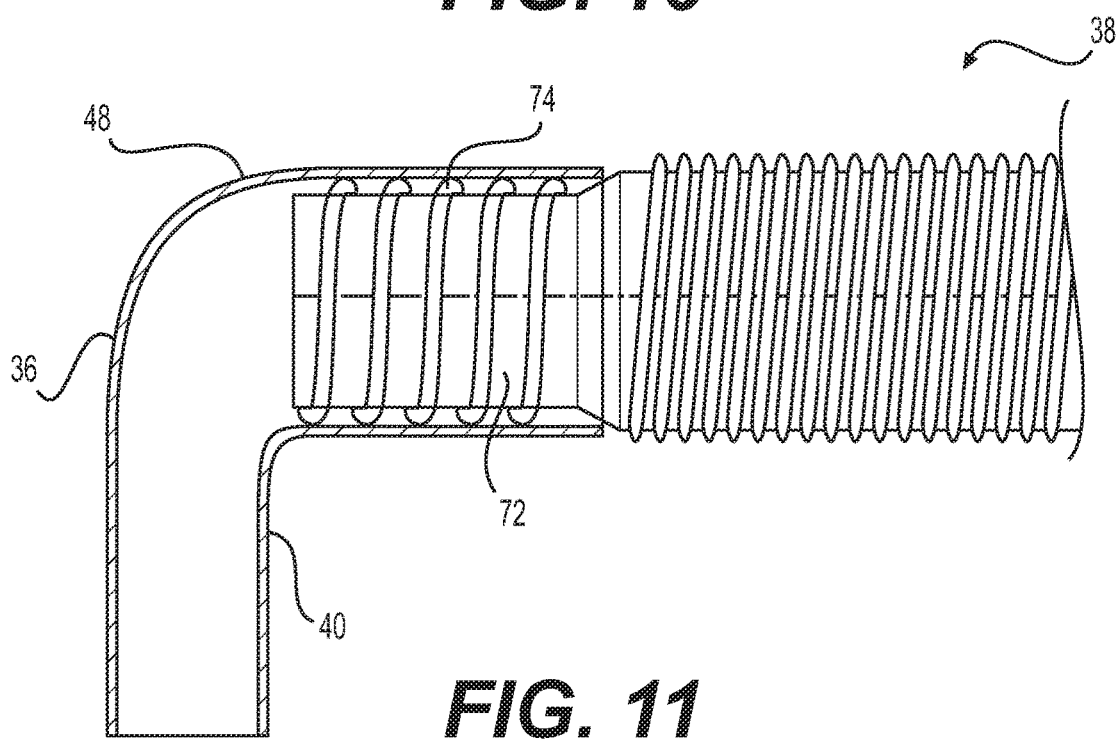
FIG. 11 is a partial sectional view of a distal end of a delivery catheter retrieving the proximal end of the capsule of FIG. 9.

Also, the helical structure of the helical wire 74 facilitates easy withdrawal, as shown in FIG. 11, into the second bend 48 of the delivery catheter 36. The helical structure can lengthen, resulting in reduction of cross-section of the capsule 38. The pitch of the capsule helical wire 74 can vary depending on the desired shortening of the capsule 38.

The tubular layer 72 can be sufficiently thin and compliant to provide for a smooth inside diameter but a protruding shape of the wire 74 on the outside diameter. This creates a ribbed appearance for the outside of the capsule 38. This configuration could also be reversed, smooth on the outside and ribbed on the inside.

Figure 12:
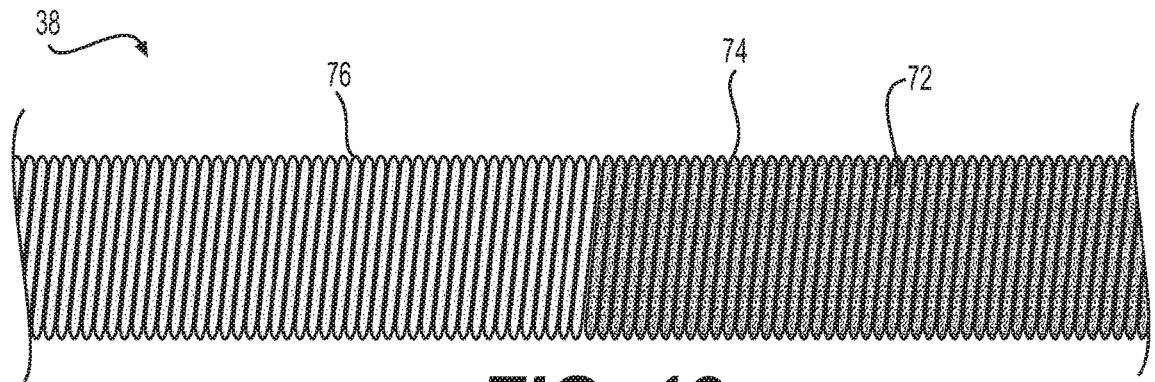
FIG. 12 is a side elevation view of the capsule of FIG. 9 abutting a proximal spring.

The delivery catheter 36 can also include a torque shaft and a proximal spring or helical wire 76 with a similar or slightly larger diameter than the diameter of the capsule 38, as shown in FIG. 12. The proximal helical wire 76 can be connected to the distal end of the torque shaft. The torque shaft (not shown) extends through the tubular structure of the delivery catheter 36 and is configured to impart torque applied at its proximal end onto distal end attachments, such as the proximal helical wire 76. The proximal helical wire 76 and torque shaft are separate from the capsule 38 to facilitate relative movement between the two. The proximal wire 76 may also be mounted on the delivery system tubular structure, behind the capsule 38, in a way that it is restricted from being torqued or moved proximally, but is still free to move distally.

Figure 13:
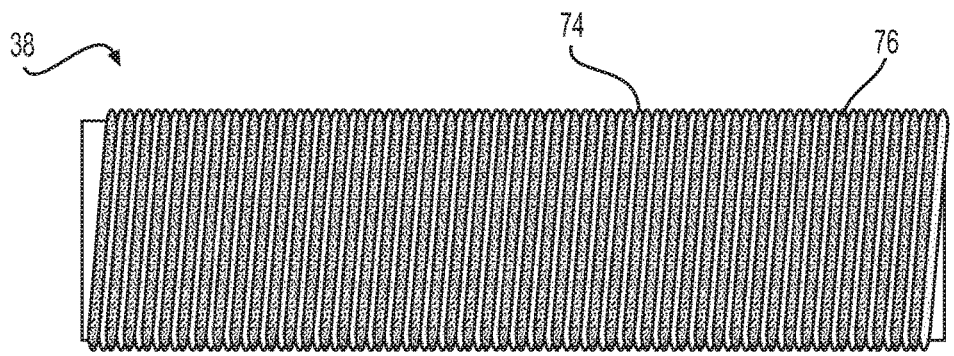
FIG. 13 is a side elevation view of the capsule and proximal spring of FIG. 12, wherein the proximal spring has been rotationally advanced into the pitch spaces of the capsule.

The proximal helical wire 76 has a wire diameter and pitch matching the helical pitch space of the capsule helical wire 74. The distal end of the proximal helical wire 76 is positioned at the proximal end of the capsule helical wire 74. Thus, rotation of the torque shaft rotates the proximal helical wire 76 and advances it into the helical pitch space, as shown in FIG. 13. Advancement of the proximal helical wire 76 into the helical pitch space of the capsule helical wire 74 progressively stiffens the capsule. As another option, the shaft attached to the capsule 38 can be rotated while pulling the capsule backwards against the proximal helical wire 76. This causes the proximal helical wire 76 to climb over the capsule 38 and the capsule can be removed through the delivery system catheter 36.

The proximal helical wire 76 can also have a tubular layer with an encapsulation similar to the capsule helical wire 74, but in a reverse configuration—the inside diameter ribbed and outside diameter smooth. In this manner, the ribbed profiles can face each other for advancement of the two coils within their respective pitches. The proximal helical wire 76 can be round or flat or other shaped cross-section wire, but with the same diameter as the pitch spaces of the capsule helical wire 74. The term "wire" as used herein is also not limited to wire of a drawn configuration—instead it could be wire cut or etched from a tube for example.

Generally, the capsule 38 of FIGS. 9 through 13 provides the ability to change the structural properties of the capsule while in use and per the needs of the procedure. Advantages of the use of the capsule helical wire 74 include the flexibility to track through the tortuous path (bends) of the delivery catheter 36 on the way to the mitral valve. The flexibility also helps in the limited room in the left atrium, where it is normally difficult to pull the capsule back in a straight line to expose the prosthetic mitral valve. Also, the capsule 38 may have an outer diameter that is the same or similar to the outer diameter of the tubular wall structure of the delivery catheter 36 and still be able to be withdrawn—thus allowing for less crimped or larger implants. Also, the capsule helical wire 74 can be compressed through a bellows effect when pulled proximally from its distal side, as shown in FIG. 10, allowing partial or full valve deployment in the tight confines of the left atrium.

After the valve is deployed, the capsule 38 is empty for pulling proximally into the catheter 36 even if it has a larger diameter. The coil configuration with the semi-compliant tubular layer 72 facilitates reduction of the capsule diameter by passively increasing the pitch distance between the coils, as shown in FIG. 11. The larger diameter capsule 38 allows delivery of larger profile implants. Further, being able to selectively stiffen the capsule, through advancement of the proximal helical wire 76, enables a "bail out" procedure where the capsule 36 is advanced back over the implant in an attempt to retrieve it.

The wires used in the helical constructions can be polymer, metal or other materials. For example, super elastic nitinol wire works particularly well given its large range of elastic strain deformation.

Figure 14:
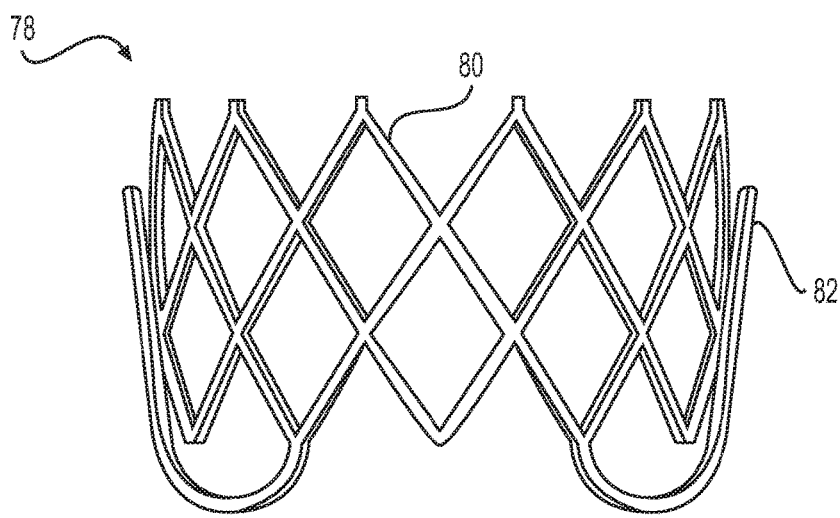
FIG. 14 is a side elevation view of a frame of a prosthetic mitral valve in a deployed configuration.
Figure 15:
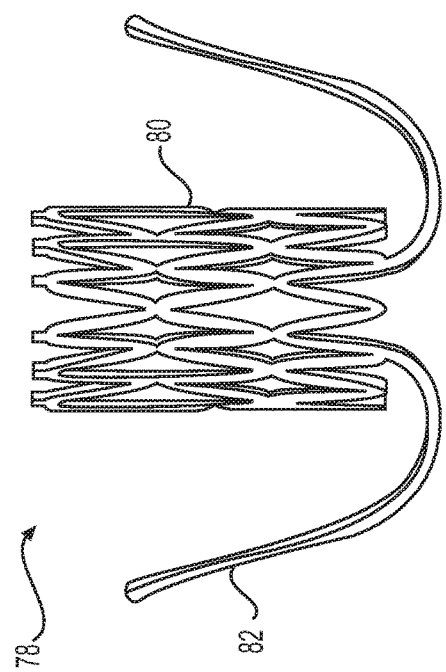
FIG. 15 is a side elevation view of the frame of FIG. 14 in a crimped configuration with paddles spaced away from a body of the frame.

FIGS. 14 and 15 show a prosthetic mitral valve frame 78 that includes a cylindrical stent body 80 and a pair of paddles 82. Generally, the paddles 82 are configured to engage or anchor into the chordae tendineae 16, as shown in FIG. 1. FIG. 14 shows the stent body 80 in the expanded configuration, wherein the paddles 82 are folded up against the outside surface of the body. FIG. 15 shows the crimped stent body 80 with the paddles 82 extending outward and spaced from an outside surface of the body.

Figure 16:
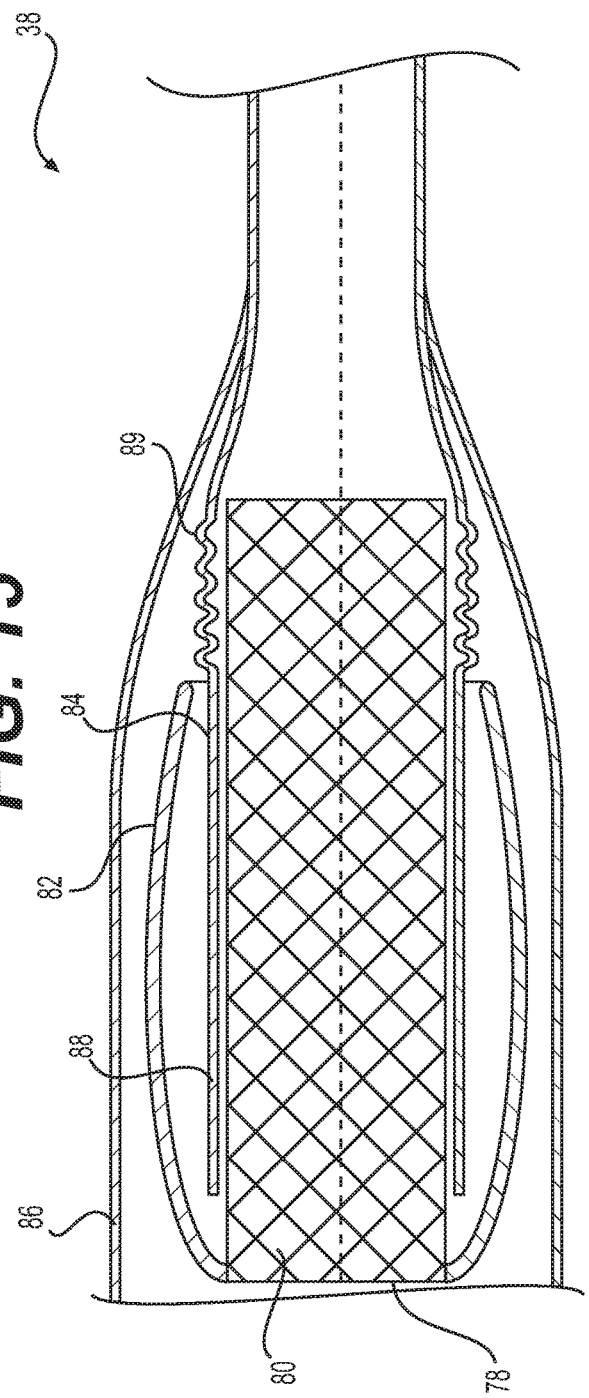
FIG. 16 is a partial sectional view of a sock-like capsule embodiment with multiple layers holding a prosthetic mitral valve in a crimped configuration.

As shown in FIGS. 16 through 18, the delivery system can include capsule 38 with multiple woven layers configured to allow sequential deployment of the paddles 82 and then the stent body 80. The multiple layers include an inner layer 84 extending around the stent body 80 and an outer layer 86 extending around the paddles 82. In the delivery configuration of FIG. 16, the inner layer 84 includes a distal portion 88 that is straight (in cross section) and cylindrical, extending directly under the paddles 82. The paddles have free ends that abut the outer surface of the inner layer 84. The inner layer also includes a proximal portion 89 that defines a crumple zone. The crumple zone includes accordion folds or other types of bunching defining a loose accumulation of the inner layer 84.

The outer layer 86 extends over the outside of the paddles 82 and, in the delivery configuration, has a free end that extends further than the free end of the inner layer 80. At a proximal end, the inner and outer layers 84, 86 are bonded, formed or otherwise coupled together to become a single layer which can be pulled to remove the multi-layered capsule 38.

FIG. 17, for example, shows a first stage of withdrawal of the capsule 38 into the distal end of the delivery catheter 36. In particular, the outer layer 86 withdraws in proportion to the length of pull on the proximal end of the capsule 38 while the distal free edge of the inner layer 84 remains static as the crumple zone of the proximal portion 89 straightens out. Movement of the outer layer 86 releases the paddles to open and engage the chordae tendineae. Then, as shown in FIG. 18, the proximal pulling of the capsule 38 finally pulls the free end of the inner layer 84 from the outside of the stent body 80 so that it can expand into place, such as within the native mitral valve annulus.

FIG. 19 shows a cross-section of capsule 38 with the crumple zone and the inner layer 84 extending around an inner shaft 90 for holding the prosthetic mitral valve (not shown). Also, the inner layer 84 and the outer layer 86 are attached to an outer shaft 91 that can be withdrawn independently of the inner shaft 90.

FIGS. 20 through 23 illustrate an embodiment of capsule 38 that uses bends in a long capsule to achieve a similar staged deployment. As shown in FIG. 20, the capsule 38 extends distally to a distal bend 92 and extends proximally from the distal bend to define an outer layer 94 (which is within an outermost layer 95). The capsule 38 continues to extend to a proximal bend 96. Then, the capsule 38 extends distally from the proximal bend 96, under the paddles 82 and over the stent body 80 to define an inner layer 98. The outer layer 94 thus restrains the paddles 82 in position and the inner layer 98 restrains the stent body 80 in its crimped position.

As shown in FIGS. 21 and 22, pulling proximally on the capsule 38 undoes the distal bend 92, and then proximal bend 96, to remove the outer layer 94 and release the paddles 82. Further pulling then retracts the remaining inner layer 98 from the stent body 80 so that it can expand into place within the mitral valve annulus.

Figure 23:
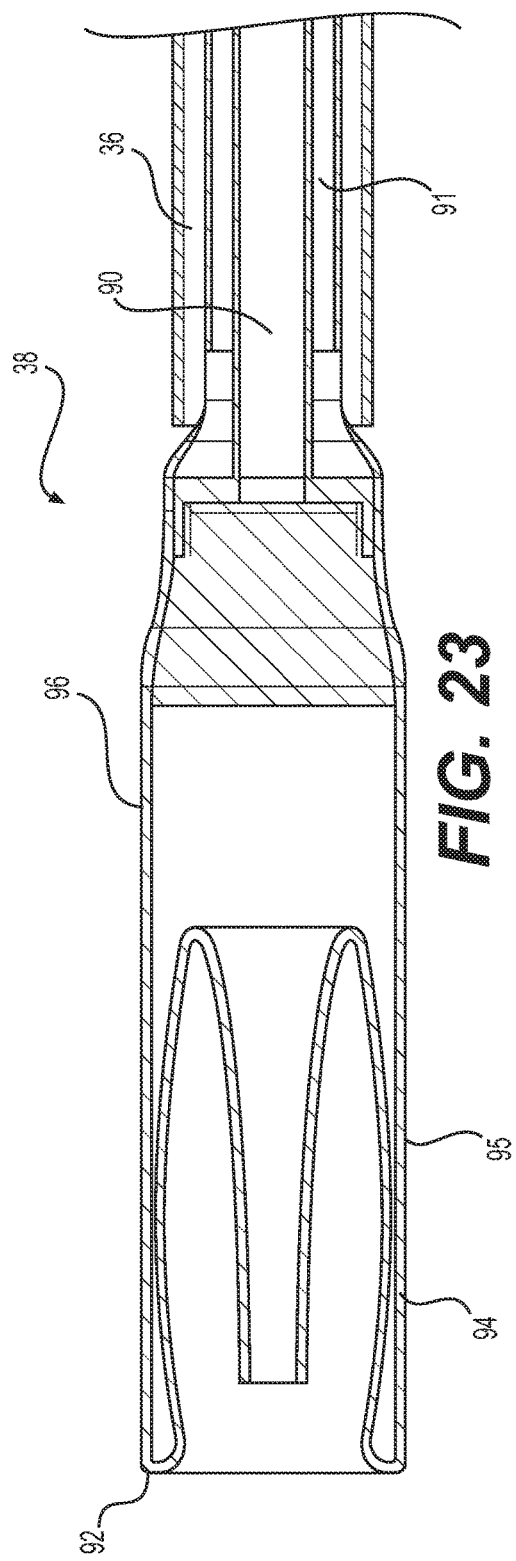
FIG. 23 is a partial sectional view of another embodiment of a capsule having bends.

FIG. 23 shows the capsule with bends 92, 96 extending around the inner shaft 90 for holding the prosthetic valve and connected to the outer shaft 91. The outer shaft 91 can be withdrawn into the delivery catheter 36 independently of the inner shaft 90 for deployment of the prosthetic valve.

Advantageously, the capsule 38 with crumple zones or bends can be retrieved back into the delivery catheter 36 without changing the delivery system position and orientation within the heart. Also, the capsule 38 can be much larger in diameter than the delivery catheter 36 because it is constructed of a flexible material, such as a fabric, and can be retrieved through smaller openings and through catheter bends. Thus, the delivery system can employ smaller profile tubular wall structures and sharper bends. The capsule material can be very thin—0.5 mm or less for example—due to the multiple layers employed. And the two-stage deployment of the prosthetic heart valve allows for more control of deployment.

Variations of the multi-layer capsule 38 include variations in diameter along the length to adapt to different valve shapes. The capsule 38 may be constructed of PET, nylon, DYNEEMA, metal wires or other flexible materials, alone and in combination.

Figure 24:
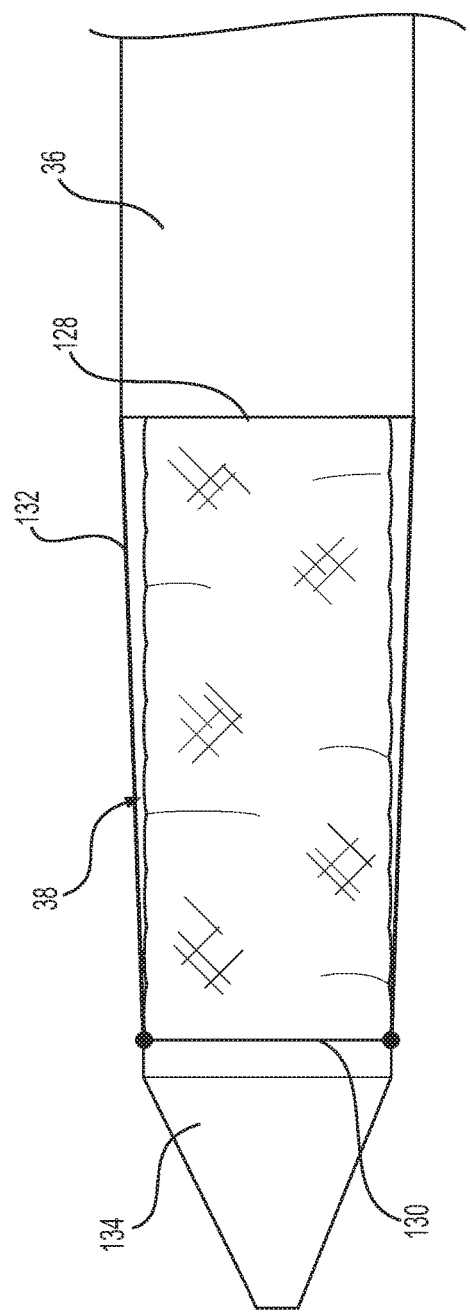
FIG. 24 is a side elevation view of another embodiment of a capsule of the present invention having a woven material in a sock-like configuration.
Figure 25:
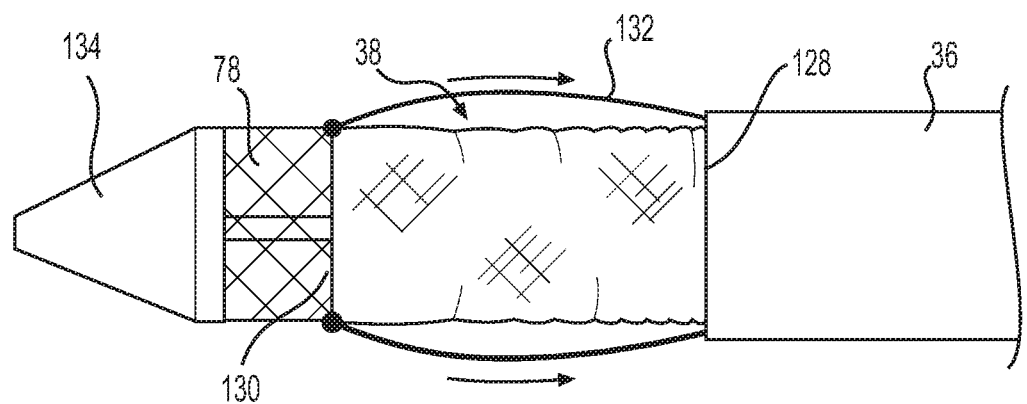
FIG. 25 is a side elevation view of the capsule of FIG. 24 being folded or bunched as it is withdrawn proximally by pulling elements.

FIGS. 24-27 show sock-like embodiments of the capsule 38 having a flexible wall material with a proximal end 128 and a distal end 130. The capsule 38 can have pull wires 132 attached to one of the ends 128, 130 so as to crumple the flexible wall material into an axially compressed state. FIGS. 24 and 25 show the pull wires 132 extending out of a distal end of the catheter 36, over the outside of capsule 38 and attaching at the distal end 130 of the capsule. The pull wires, when pulled, crumple up the capsule 38 as the distal end 130 retracts back toward the proximal end 128 to reveal the underlying prosthetic mitral valve with minimal friction forces. The sock-like crumpling avoids the capsule friction against the inside of the delivery catheter and along the outside of the prosthetic mitral valve.

Figure 26:
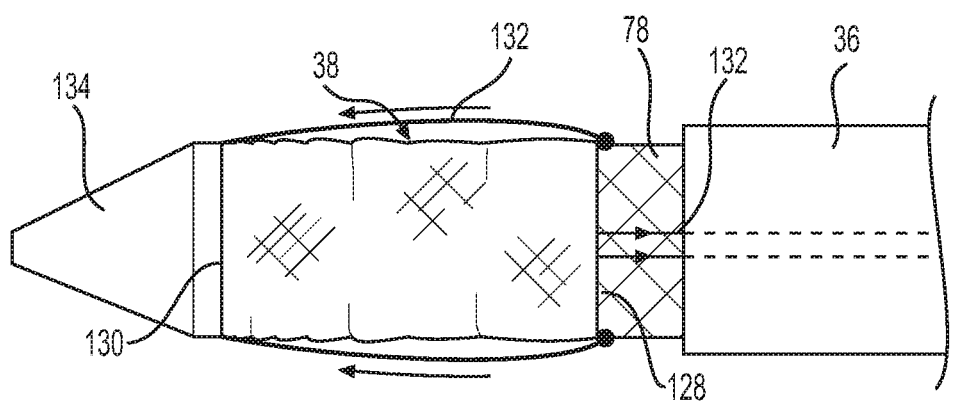
FIG. 26 is a side elevation view of another sock-like capsule embodiment having pulling elements extend through a nose cone for folding the capsule in the distal direction.
Figure 27:
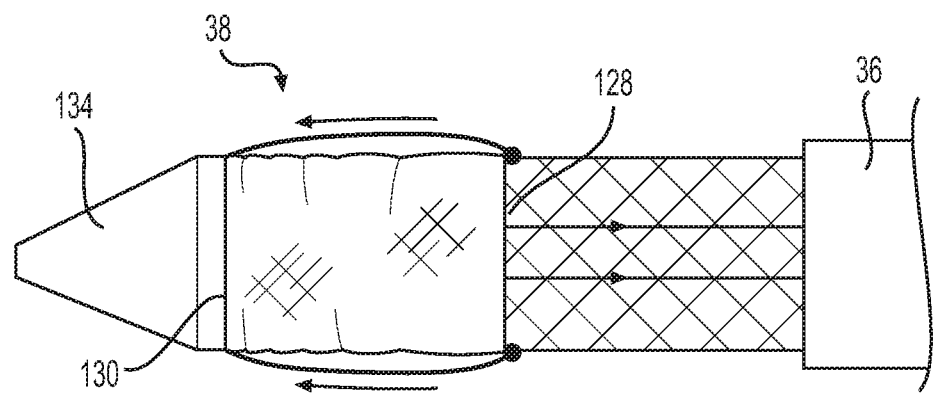
FIG. 27 is a side elevation view of the capsule of FIG. 26 progressively folding in the distal direction to release a prosthetic valve for expansion.

The pull wires 132 may also interact with a nosecone 134. FIGS. 26 and 27 show an embodiment wherein the pull wires are connected to the proximal end 128, extend distally to wrap around a feature (e.g., a pulley or post) inside a nosecone 134 to double-back through a center of the prosthetic mitral valve to the proximal end of the delivery catheter 36. Pulling on the pull wires 132 moves the proximal end 128 toward the distal end 130, crumpling up the sock-like capsule 38. This configuration advantageously allows the proximal end of the prosthetic valve to expand first, which can be advantageous for deployments in the direction of blood flow. The proximal end of the valve can expand as an anchor.

Figure 28:
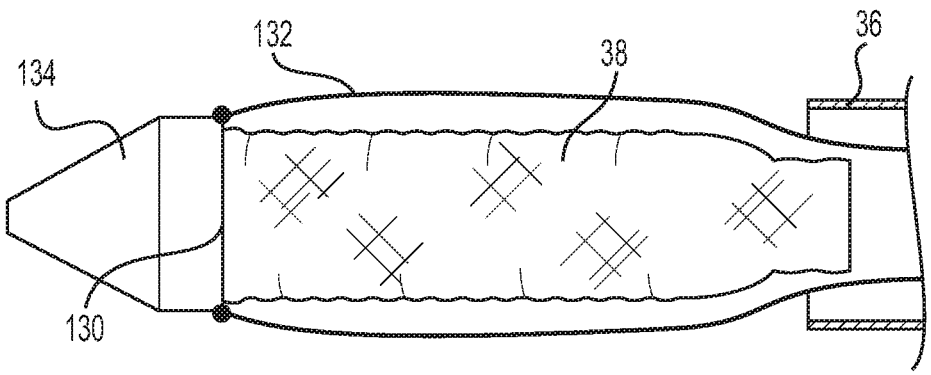
FIGS. 28-29 are schematics of a standalone, sock-like capsule of another embodiment of the present invention.
Figure 29:
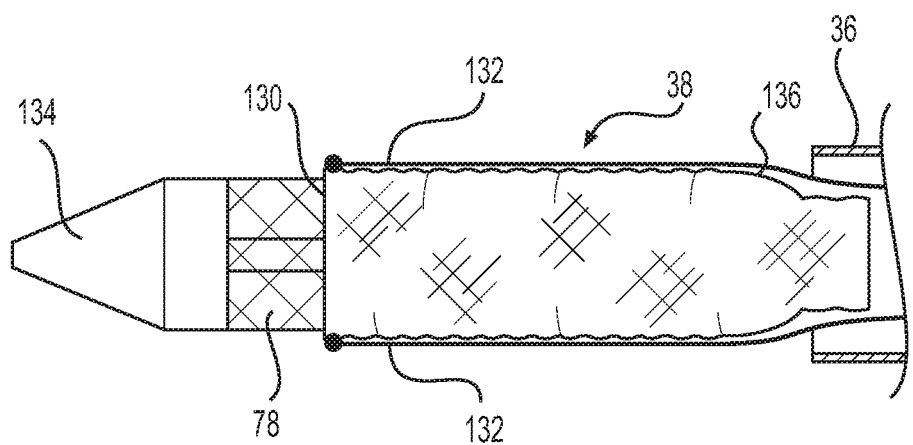

FIGS. 28 and 29 illustrate an alternative embodiment of the capsule 38 wherein the capsule is not connected to the delivery catheter 36. Instead, the capsule 38 is a standalone flexible, woven capsule with pull wires 132 connected to its distal end 130, as shown in FIG. 28. The capsule includes a tapered configuration 136 at its proximal end that is sized to fit in the distal end of the tubular wall structure of the delivery catheter 36. The prosthetic valve can be crimped into the standalone capsule 38.

FIG. 28 shows the capsule 38 with the prosthetic valve mounted on the delivery catheter 36, including the nosecone 134 applied to the distal end of the assembly. FIG. 29 shows the pull wires 132 being pulled back to fold the capsule 38 into a crumpled, sock-like configuration to deploy the prosthetic valve. Advantageously, the standalone capsule 38 does not need a proximal support, reducing the working length of the assembly within the left ventricle.

The sock-like capsules 38 can have varying diameters to adapt them to the shape of different types of implants.

Other advantages of the sock-like capsule 38 configurations include low deployment forces. Only pulling one end of the tube generates less friction than pulling the whole woven tube over the prosthetic valve. In contrast, conventional pulling of the whole capsule generates friction between the capsule surface and the entire prosthetic valve. For sock-like capsules, the pulling point at one end only peels the capsule off the valve frame with folding, rather than relative sliding. Another advantage includes wire pulling through the nosecone 134, reducing or eliminating the need for the nosecone to move forward toward the apex of the left ventricle. This can reduce the risk of chordae entanglement.

The sock-like capsule 38 can also simplify the valve crimping process and reduce the delivery system profile. Only wires without a pulling tube need to go through the delivery catheter 36. Also, the capsule 38 can be retrieved back into the delivery catheter by folding, thus not requiring the delivery system position and orientation to change within the heart. Generally, also, capsules comprised of flexible, foldable materials can be easily reduced in diameter and can be pulled through sharp bends can be much larger in diameter.

In view of the many possible embodiments to which the principles of the disclosed invention can be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A system for treating a defective native heart valve, comprising:
    a catheter configured to extend through the vasculature and having a distal end for positioning in proximity to the native heart valve;
    an expandable prosthetic heart valve coupled to the distal end of the catheter for placement within the native heart valve;
    a flexible capsule defining a lumen configured to contain the prosthetic heart valve and including a tubular layer and a capsule helical wire attached to and encircling the tubular layer, wherein the capsule helical wire has a helical pitch space defined between adjacent windings of the capsule helical wire;
    a torque shaft having a proximal end and a distal end; and
    a proximal helical wire coupled to the distal end of the torque shaft, wherein the proximal helical wire has a diameter and pitch matching the helical pitch space and wherein rotation of the proximal end of the torque shaft rotates the proximal helical wire and axially advances the proximal helical wire into the pitch space of the capsule helical wire so as to stiffen the capsule for retrieval of the prosthetic heart valve into the lumen.

2. The system of claim 1, wherein the tubular layer includes a thin polymer encapsulating the capsule helical wire.

3. The system of claim 2, wherein the helical pitch space is defined on an outside surface of the tubular layer.

4. The system of claim 3, wherein an inside surface of the tubular layer is smooth.

5. The system of claim 4, further comprising a delivery sheath having a lumen containing the proximal end of the catheter, wherein the capsule helical wire is configured to reduce in diameter for withdrawal of the flexible capsule into the lumen of the delivery sheath.

6. The system of claim 1, further comprising an elongate puller coupled to a distal end of the flexible capsule and configured to pull the proximal end of the flexible capsule to reduce the helical pitch space and reveal the prosthetic heart valve.

* * * * *